United States Patent
Hao et al.

(10) Patent No.: US 7,780,602 B2
(45) Date of Patent: Aug. 24, 2010

(54) METHOD AND SYSTEM FOR CONTROLLING AN ULTRASOUND SYSTEM

(75) Inventors: Xiaohui Hao, Redmond, WA (US); Kirstin Nora LaConte, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 744 days.

(21) Appl. No.: 11/023,008

(22) Filed: Dec. 27, 2004

(65) Prior Publication Data

US 2006/0173311 A1     Aug. 3, 2006

(51) Int. Cl.
*A61B 8/14*     (2006.01)
(52) U.S. Cl. .................. 600/458; 600/437; 600/443; 600/448; 73/625; 73/626
(58) Field of Classification Search ......... 600/442–458, 600/437, 420, 408, 431; 601/1–2; 73/625, 73/626
See application file for complete search history.

(56) References Cited

U.S. PATENT DOCUMENTS

| | | | | |
|---|---|---|---|---|
| 5,482,046 | A * | 1/1996 | Deitrich | 600/458 |
| 6,042,556 | A * | 3/2000 | Beach et al. | 601/3 |
| 6,413,218 | B1 * | 7/2002 | Allison et al. | 600/443 |
| 6,488,639 | B1 * | 12/2002 | Ribault et al. | 601/2 |
| 6,714,667 | B1 * | 3/2004 | Mooney et al. | 382/128 |
| 6,899,681 | B1 * | 5/2005 | Phillips et al. | 600/458 |

* cited by examiner

*Primary Examiner*—Brian Casler
*Assistant Examiner*—John F Ramirez
(74) *Attorney, Agent, or Firm*—Dean Small; Small Patent Law Group (57) ABSTRACT

Methods and system for controlling an ultrasound system are described. One method includes acquiring ultrasound data relating to an object and iteratively adjusting acoustic power output of the ultrasound system based on the acquired ultrasound data.

17 Claims, 5 Drawing Sheets

METHOD AND SYSTEM FOR CONTROLLING AN ULTRASOUND SYSTEM

BACKGROUND OF THE INVENTION

The invention relates generally to ultrasound imaging systems, and more particularly, to contrast imaging systems.

Contrast imaging scanning is an ultrasound technique used for various clinical studies. For example, it may be used to study the flow of blood through a body of a patient who is to be scanned. Contrast imaging includes injecting contrast agents in the body of the patient. The injected contrast agents provide a better visualization of blood flow, for example, in the study of flow of blood.

Contrast agents for ultrasound imaging typically include encapsulated gas bubbles that have a diameter less than ten microns. These bubbles enhance the amplitude of back-scattered ultrasound signals. The back-scattered ultrasound signals are the ultrasound signals that return back after getting reflected from the parts of the body being scanned. The enhanced amplitude results from bubble reflection and/or bubble destruction. The amplitude of the ultrasound signal is enhanced as the ultrasound signal is reflected from an interface between two objects or materials, for example, from the interface of tissues and contrast agents. Bubble destruction inside the body of the patient also enhances the amplitude of the back-scattered ultrasound signals. The amount of reflection and bubble destruction depends on the power of the ultrasound signals. The power of the ultrasound signals is often referred to as an acoustic power output of the ultrasound signals. Acoustic power output is usually measured as the amount of ultrasound energy delivered per unit time. The acoustic power output further may be represented or defined by a Mechanic Index (MI) value.

A low MI value (e.g., MI<0.2) enhances amplitude through reflection. A high MI value (e.g., MI>0.2), however, enhances amplitude through bubble destruction. Bubble destruction can result in an intermittent scan. Intermittence is introduced as new bubbles need to be injected when bubbles are destroyed. Therefore, for uninterrupted scanning, low MI value contrast imaging with minimum bubble destruction is typically used.

Generally, in a contrast imaging scan, the MI value of the ultrasound signals is set before injecting the contrast agents in the body. However, the ultrasound signals can get attenuated as they travel through the body of the patient. Hence, the resultant MI value of the ultrasound signal inside the body may be less than the preset value. Further, the amount of attenuation in the MI value depends on the characteristics of the body. For example, the MI value depends on the amount of fat in the body as the attenuation of the ultrasound signals is greater in a fat layer compared to muscles. Therefore, when the amount of fat in the body is high, the MI value of the ultrasound signal inside the body is less.

In order to maintain the required MI value in the body, doctors adjust the setting of the MI value during a contrast imaging scan. However, this adjustment is performed manually and may lead to important information getting lost while the setting is adjusted. For example, for the scanning of a liver tumor, the first few seconds in an artery phase ultrasound scan are very important.

BRIEF DESCRIPTION OF THE INVENTION

In one exemplary embodiment, a method for controlling an ultrasound system is provided. The method includes acquiring ultrasound data relating to an object. The method further includes iteratively adjusting an acoustic power output of the ultrasound system based on the acquired ultrasound data relating to the object.

In another exemplary embodiment, an ultrasound system is provided. The ultrasound system includes a scanning portion for scanning an object. The ultrasound system further includes a control portion that is configured to automatically control an acoustic power output of the scanning portion based on the object being scanned.

DETAILED DESCRIPTION OF THE INVENTION

Various embodiments of the invention provide methods and systems for controlling an ultrasound system. In accordance with various embodiments of the invention, the ultrasound system is used for performing contrast imaging scans. Contrast imaging scanning is an ultrasound technique in which contrast agents are used. The contrast agents may include, for example, encapsulated gas bubbles, also called contrast bubbles or contrast microbubbles, having a diameter of less than ten microns. These bubbles enhance the amplitude of back-scattered ultrasound signals. The back-scattered ultrasound signals are the ultrasound signals that return back after getting reflected from the parts of the body being scanned.

The various embodiments of the invention minimize the destruction of the contrast agents, and in particular, the contrast bubbles. This is achieved by adjusting an acoustic power output for an ultrasound system. The acoustic power output may be expressed or defined as the ultrasound energy delivered per unit time. A Mechanic Index (MI) value is a measure of the acoustic power output of the ultrasound system. The MI value may be calculated by dividing the peak rarefactional pressure of a longitudinal ultrasonic pulse by the central frequency of the longitudinal ultrasonic pulse.

Figure 1:
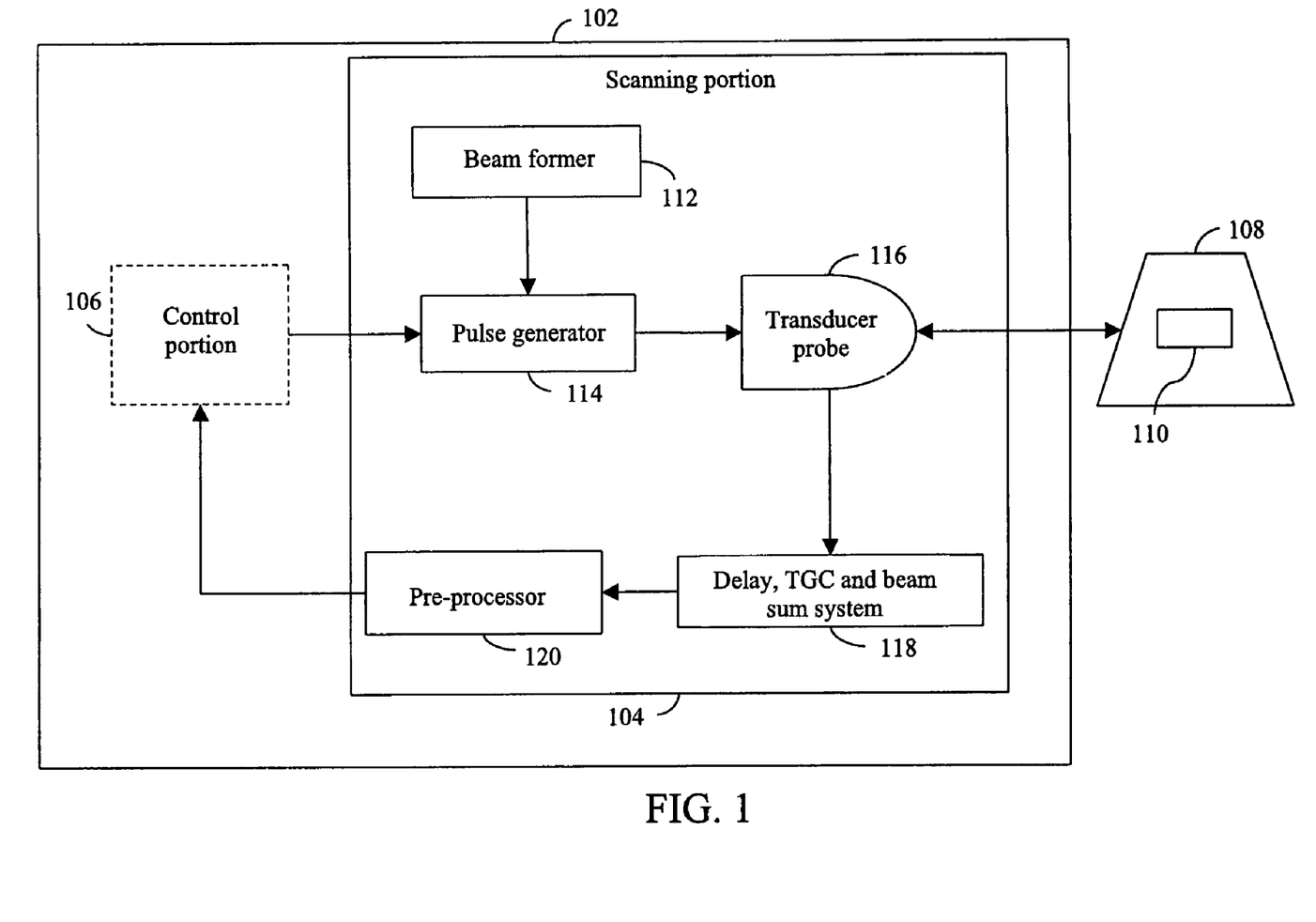
FIG. 1 is a block diagram of an ultrasound system in accordance with various embodiments of the invention.

FIG. 1 is a block diagram of an ultrasound system 102 in accordance with various embodiments of the invention. Ultrasound system 102 includes a scanning portion 104 and a control portion 106. Scanning portion 104 is used to scan an object 108 and acquire ultrasound data relating to object 108. Object 108 is the entire area that is being scanned by scanning portion 104. This means that during the scan, an image of object 108 is obtained. Object 108 may be, for example, a human or a part of a human, such as a liver. In accordance with various embodiments of the invention, a Region Of Interest (ROI) 110 is a smaller part of object 108 which a user may be interested in scanning. The user may be, for example, a doctor who is scanning object 108. In accordance with various embodiments of the invention, the user can select ROI 110 from the image of object 108. For example, if the user is interested in scanning only left lobe of the liver, then the user can select the left lobe as ROI 110.

Acquiring the ultrasound data includes transmitting an ultrasound beam into object 108 and receiving signals back-scattered from object 108 as is known. The ultrasound beam is a narrow beam of ultrasound signals. As the ultrasound beam travels through object 108, various parts of object 108 reflect and backscatter the ultrasound signals.

Scanning portion 104 also includes a beam former 112, a pulse generator 114, a transducer probe 116, a delay, time gain compensation (TGC) and beam sum system 118 and a pre-processor 120. Beam former 112 controls the direction and focus of the ultrasound beam that is used for scanning object 108. Based on the direction and focus of the ultrasound beam as determined by beam former 112, pulse generator 114 generates electric pulses. Pulse generator 114 also receives signals from control portion 106. These signals define the value of current or voltage for the electric pulses. These electric pulses are transmitted to transducer probe 116, which generates an ultrasound beam based on the electric pulses. The current or voltage of the electric pulses defines the acoustic power output of the ultrasound beam. For example, if the current or voltage of the electric pulses is increased, the acoustic power output of the ultrasound beam will increase.

The ultrasound beam generated by transducer probe 116 is transmitted into object 108. The ultrasound beam is reflected and back-scattered as it travels through object 108. Back-scattered signals are received by transducer probe 116.

Delay, TGC and beam sum system 118 delays the received back-scattered signals, such that the back-scattered signals are steered and focused. Delay, TGC and beam sum system 118 further amplifies the back-scattered signals to compensate for the attenuation of the ultrasound beam. Finally the delayed and amplified signals are summed by delay, TGC and beam sum system 118 to obtain a radio frequency (RF) signal. The RF signal is partially processed data in ultrasound system 102.

Pre-processor 120 then further processes the RF signal. Examples of processing applied to the RF signal include, but are not limited to, and as is known, demodulation, Hilbert transforming and band pass filtering. Demodulation is the process of extraction of low-frequency signals from the RF signal. Hilbert transforming is performed by shifting the phase of a signal by a fixed unit. This is done to obtain a double signal for complex processing. In band pass filtering, only signals with a frequency within a pre-specified range are filtered through or can pass through to the control portion, with other signals rejected or filtered out. This reduces the noise in the received signal. The above are examples of processing and are not exclusive and further processing of RF signal may be performed. The processed signal is then provided to control portion 106. In accordance with various embodiments of the invention, the RF signal can also be used by control portion 106 without being first processed by pre-processor 120.

Based on the received signal, (e.g., RF or processed RF signal), control portion 106 controls the acoustic power output of ultrasound system 102. Control portion 106 accordingly sends a signal to pulse generator 114. This signal defines the value of current or voltage corresponding to which pulse generator 114 generates electric pulses. In accordance with various embodiments of the invention, control portion 106 controls the acoustic power output of ultrasound system 102 by iteratively sending the signal to pulse generator 114. Control portion 106 is described in detail with reference to FIG. 2.

Figure 2:
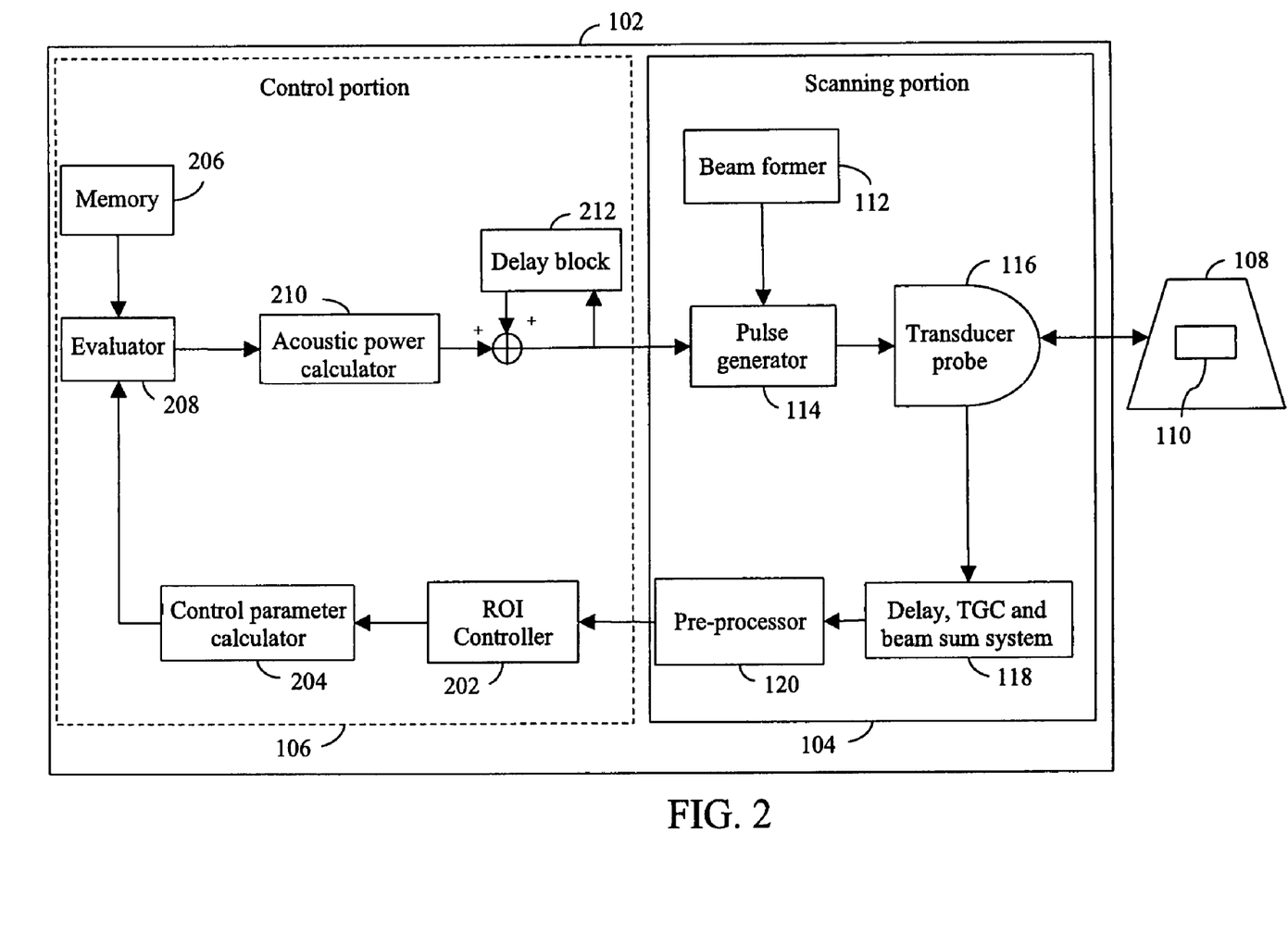
FIG. 2 is a detailed block diagram showing a control portion of an ultrasound system in accordance with various embodiments of the invention.

FIG. 2 is a detailed block diagram showing control portion 106 of ultrasound system 102 in accordance with various embodiments of the invention. Control portion 106 includes an ROI controller 202, a control parameter calculator 204, a memory 206, an evaluator 208, an acoustic power calculator 210 and a delay block 212. ROI controller 202 controls the selection and definition of ROI 110 in object 108. For example, while scanning a patient, a doctor can define ROI 110 to be a part of a human liver using ROI controller 202. In one embodiment of the invention, ROI controller 202 displays an image representing an ultrasound scan on a screen. The user then defines ROI 110 by selecting a portion of the displayed image. ROI controller 202 then extracts signals specific to ROI 110 from the received RF signal.

Based on the extracted signals, control parameter calculator 204 calculates at least one control parameter. It should be noted that ROI controller 202 may or may not be used. Control parameter calculator 204 directly receives the RF signal. Hence, signals corresponding to the whole object 108 are used to calculate the control parameter. Examples of control parameters include an averaged acoustic intensity value in ROI 110, an average acoustic intensity value, a root mean square acoustic intensity value and an average MI value. The averaged acoustic intensity value in ROI 110 is calculated by taking an arithmetic average of acoustic intensity values of the back-scattered signals specific to ROI 110, as extracted by ROI controller 202. The average acoustic intensity value is an arithmetic average of acoustic intensity values of the back-scattered signals corresponding to object 108. The root mean square acoustic intensity value is calculated by summing the squares of acoustic intensity values of the back-scattered signals and then taking a square root of the sum. The average MI value is an arithmetic average of MI values of the back-scattered signals.

To control ultrasound system 102, the calculated value of the control parameter is compared to a threshold value related to the control parameter. The threshold value is stored in memory 206 (e.g., in a lookup table). Evaluator 208 compares the calculated control parameter and the threshold value and determines if the calculated control parameter is greater than the threshold value. Based on this comparison, a difference ($\Delta CP$) between the calculated control parameter and the threshold value is calculated. Corresponding to the calculated $\Delta CP$, acoustic power calculator 210 calculates a difference in acoustic power output ($\Delta AO$). $\Delta AO$ can be calculated from $\Delta CP$, for example, by using an empirical relationship between the acoustic power output and the control parameter. The empirical relationship may be developed by measuring the acoustic power output and the corresponding value of the control parameter for a sample of patients.

Delay block 212 receives the signal sent by control portion 106 to pulse generator 114. Pulse generator 114 uses this signal to define the value of acoustic power output of the ultrasound beam. $\Delta AO$ is added to this received signal to generate a new signal. The new signal defines a new value of acoustic power output for the ultrasound beam. The new value of acoustic power output is provided to scanning portion 104. Hence, scanning portion 104 acquires feedback information from control portion 106. Based on the obtained feedback, scanning portion 104 automatically sets the new value of acoustic power output for scanning object 108. In accordance with various embodiments of the invention, the feedback information is the new value of acoustic power output. The new value of acoustic power output is used to adjust the MI value of the ultrasound beam.

Figure 3:
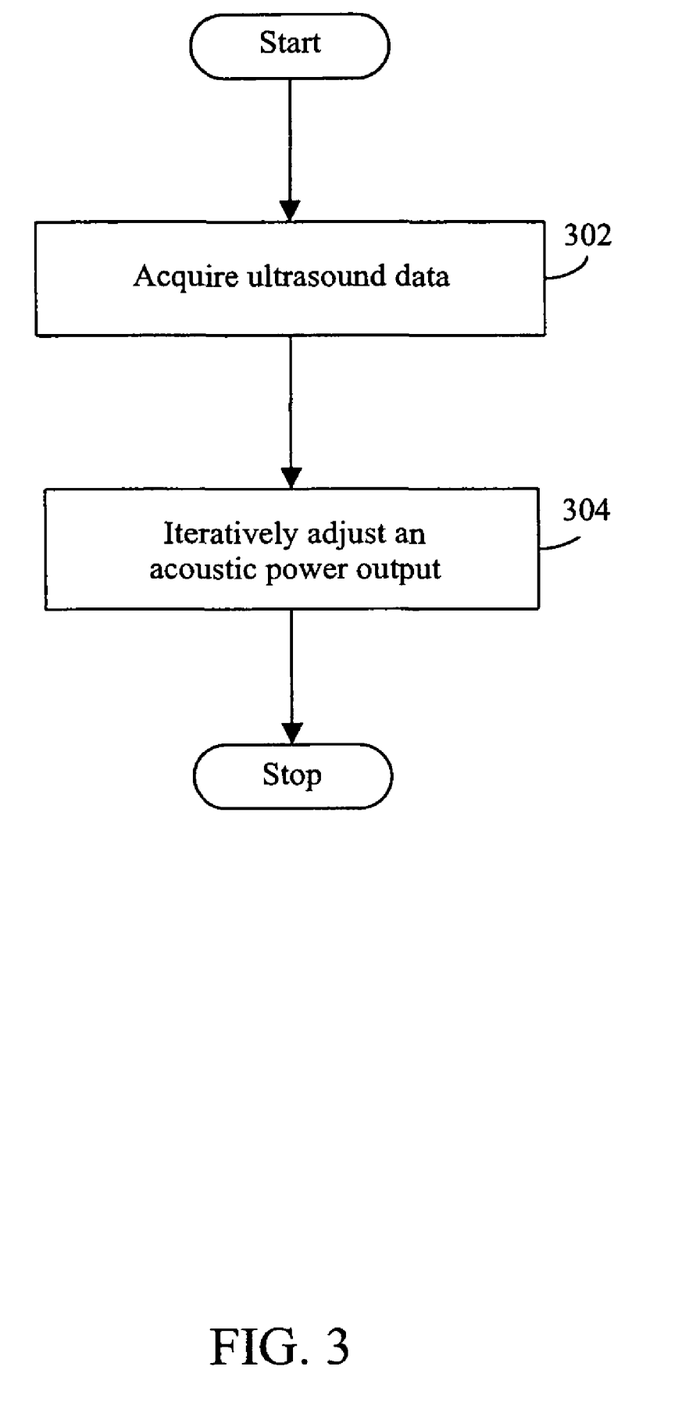
FIG. 3 is a flowchart of a method for controlling an ultrasound system in accordance with various embodiments of the invention.

FIG. 3 is a flowchart of a method for controlling ultrasound system 102 in accordance with various embodiments of the invention. At 302, scanning portion 104 acquires ultrasound data related to object 108. For example, transducer probe 116 transmits the ultrasound beam into object 108 to acquire ultrasound data. The signals in the ultrasound beam are reflected and back-scattered. Transducer probe 116 then receives the back-scattered signal. The back-scattered signal includes ultrasound data related to object 108. In accordance with various embodiments of the invention, the ultrasound data includes contrast imaging data. For this purpose, scanning portion 104 is held at a contrast imaging setting while the ultrasound data is being acquired. Contrast imaging setting means that all the functions associated with contrast imaging scan are performed, however, the contrast agents are not injected into object 108.

At 304, the acoustic power output of ultrasound system 102 is adjusted iteratively. The acoustic power output is automatically adjusted, based on the acquired ultrasound data. This process is repeated until the value of acoustic power output falls below a threshold value for acoustic power output. The automatic adjustment is based on at least one characteristic of object 108, for example, the amount of fat in object 108. The acoustic power output is adjusted to automatically adjust the MI value corresponding to the object 108. The adjusted acoustic power output is provided such that the destruction of contrast bubbles in object 108 is minimized. Feedback information is provided to adjust the acoustic power output. In accordance with an embodiment of the invention, the feedback information includes the acquired ultrasound data and the average MI value in ROI 110.

Figure 4:
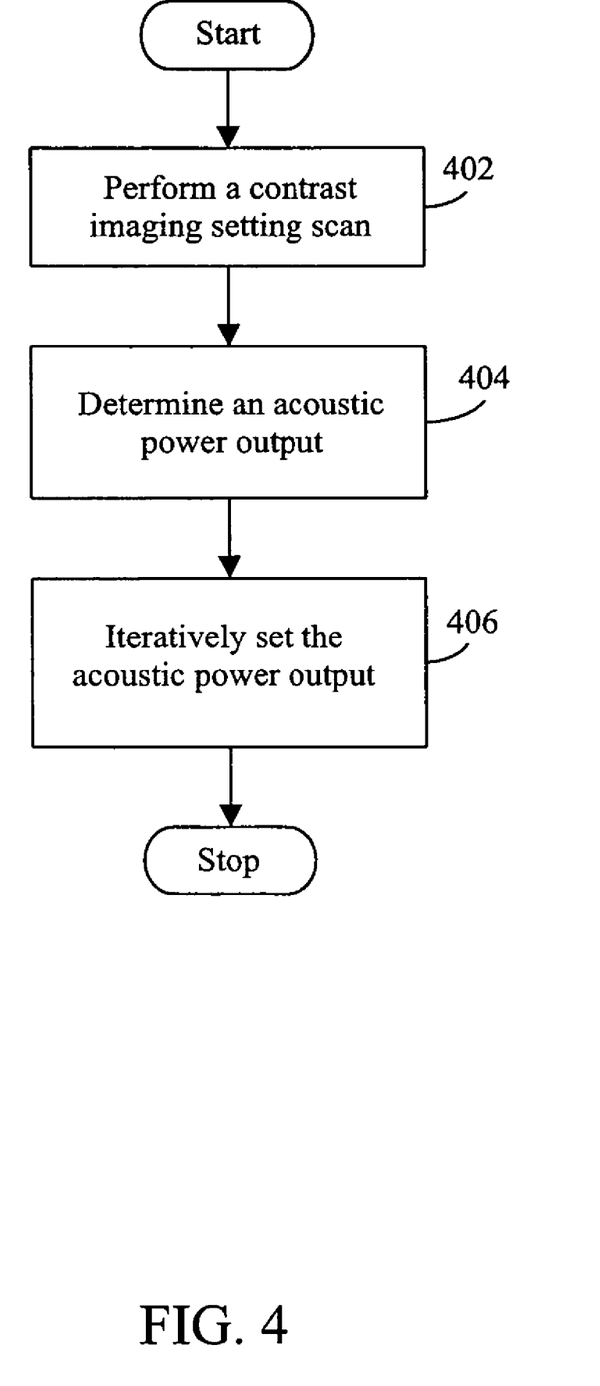
FIG. 4 is a flowchart of another method for controlling power in an ultrasound system in accordance with various embodiments of the invention.

FIG. 4 is a flowchart of another method for controlling power in ultrasound system 102 in accordance with an exemplary embodiment of the invention. At 402, a contrast imaging setting scan of object 108 is performed. In accordance with various embodiments of the invention, the ultrasound data specific to ROI 110 is extracted each time a scan with contrast imaging setting is performed. At 404, a new value of acoustic power output is determined based on the extracted ultrasound data. The determination of the new value of acoustic power output is described in detail with reference to FIG. 5. At 406, ultrasound system 102 iteratively sets the acoustic power output to the determined new value.

In accordance with various embodiments of the invention, the contrast imaging setting scan is performed iteratively to determine, for example, an optimal value of acoustic power output to reduce the possibility of contrast agent bubble destruction in an object being scanned. The contrast imaging scan is completed by injecting the contrast agents into object 108 at the optimal value of acoustic power output.

Figure 5:
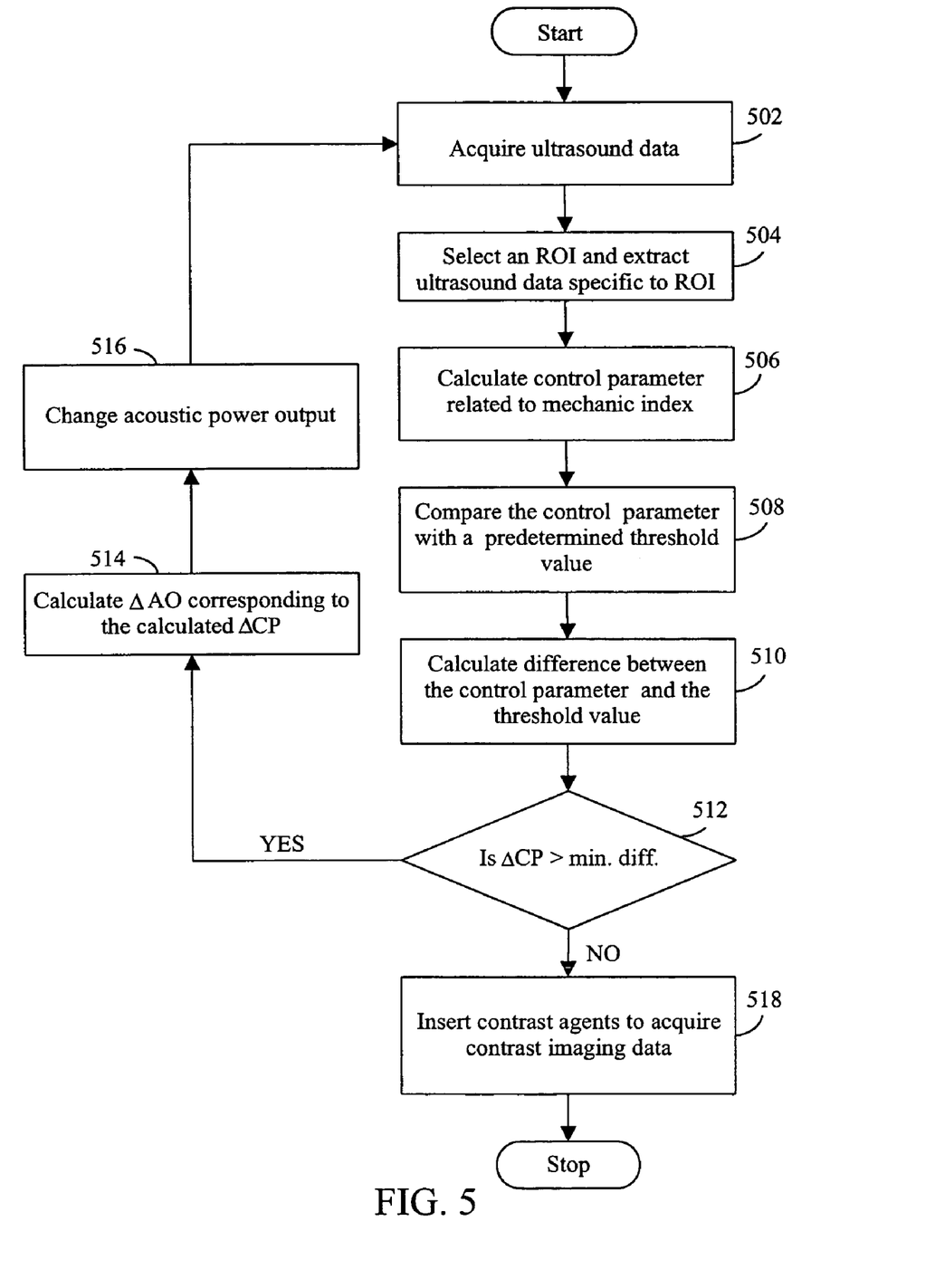
FIG. 5 is a flowchart of another method for controlling an ultrasound system in accordance with an exemplary embodiment of the invention.

FIG. 5 is a flowchart of another method for controlling ultrasound system 102 in accordance with an exemplary embodiment of the invention. At 502, scanning portion 104 acquires ultrasound data related to object 108. The acquired ultrasound data includes data related to the MI value of the back-scattered signals. The ultrasound data is acquired by performing a first scan of object 108.

At 504, the user selects ROI 110. Further, in accordance with various embodiments of the invention, a part of the ultrasound data specific to ROI 110 is extracted at 504. A global gain is applied to the extracted ultrasound signal. The global gain is a static number applied to all intensity values in the back-scattered signals.

At 506, at least one control parameters related to the MI value is calculated. The control parameters include, for example, the average acoustic intensity value in ROI 110, the average acoustic intensity value, the average MI value and the root mean square acoustic intensity value. At 508, the calculated control parameter is compared with a threshold value to determine if the calculated control parameter is greater than the threshold value. For example, the calculated average intensity value can be compared with a predetermined threshold value for the average acoustic intensity value. The threshold value is established, for example, by the user or by ultrasound system 102. The threshold value can also be a predetermined value. In accordance with various embodiments of the invention, the threshold value is determined from clinical analysis of a plurality of objects having different characteristics. One such characteristic is, for example, the amount of fat in the objects. The threshold value is selected such that the acoustic power output corresponding to the threshold value results in minimum destruction of the contrast bubbles in object 108.

Based on the comparison, a difference between the calculated value and the threshold value is calculated at 510. The calculated difference is referred to as ΔCP. At 512, the calculated ΔCP is compared with a minimum difference value. In accordance with various embodiments of the invention, the minimum difference value is specified by the user. If ΔCP is greater than the minimum difference value, a difference in acoustic power output is calculated at 514 and this is termed as ΔAO. At 516, the value of acoustic power output for a next scan is changed by adding ΔAO to the value of acoustic power output of the first scan. For example, if the calculated average intensity value is greater than the threshold value, the current or voltage of the electric pulses generated by pulse generator 114 is decreased accordingly. The adjusted value of acoustic power output is used to acquire ultrasound data by performing a second scan at 502. This process of adjusting acoustic power output is performed iteratively until ΔCP is less than the minimum difference value. In accordance with various embodiments of the invention, the value of acoustic power output is adjusted iteratively until the value of control parameter is less than the threshold value. In accordance with various embodiments of the invention, during the second scan, the user may not select ROI 110 at 504. ROI controller 202 automatically extracts signals specific to ROI 110 as selected by the user during the first scan.

The value of acoustic power output at which ΔCP is less than the specified minimum difference value is the optimal value of acoustic power output. If ΔCP is less than the minimum difference value, contrast agents are injected into object 108 at 518. After the injection, the contrast imaging scan is performed to obtain an image of object 108.

The various embodiments of the invention provide an adaptive contrast imaging system. The setting of contrast imaging is performed automatically and ultrasound system 102 provides the same quality of contrast image for patients with different characteristics. In addition, the setting of contrast imaging is adjusted such that there is minimum destruction of contrast bubbles in the body of the patient. Therefore, the contrast bubbles are available even if some bubbles are destroyed. Because the setting of contrast imaging is performed automatically, doctors do not have to adjust the setting manually during scanning. Hence, the productivity of the hospitals can be increased, while ensuring good quality images.

A technical effect of the various embodiments of the invention is to automatically adjust the value of acoustic power output of ultrasound system 102 to an optimal value. The adjustment is performed by comparing a control parameter with a threshold value. This comparison is repeated iteratively until the value of the acoustic power output is less than the threshold value.

The various embodiments or components thereof may be implemented as part of a computer system. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A method for controlling an ultrasound system, said method comprising:
    acquiring ultrasound data relating to an object; and
    iteratively adjusting, before injecting a contrast agent into the object, an acoustic power output of the ultrasound system based on the acquired ultrasound data relating to the object, wherein iteratively adjusting the acoustic power output comprises determining a difference in the acoustic power output and adjusting the acoustic power output based on the determined difference.

2. A method in accordance with claim 1 wherein the ultrasound data comprises contrast imaging data.

3. A method in accordance with claim 1 wherein the object comprises a human and wherein the acoustic power output is adjusted based on at least one characteristic of the human.

4. A method in accordance with claim 1 further comprising receiving from an ultrasound scan in a contrast imaging mode feedback information, including the acquired ultrasound data, relating to a region of interest of the object.

5. A method in accordance with claim 1 further comprising establishing a threshold value for a control parameter related to acoustic power output and wherein iteratively adjusting the acoustic power output comprises:
    determining an actual value of the control parameter based on the acquired ultrasound data;
    comparing the actual value of the control parameter with the threshold value;
    adjusting the acoustic power output based on a difference between the actual value and the threshold value of the control parameter; and
    repeating the determining, comparing, and adjusting steps until a predetermined relationship between the actual value and the threshold value of the control parameter is met.

6. A method in accordance with claim 5 wherein the threshold value is determined based on clinical analysis.

7. A method in accordance with claim 5 wherein the control parameter comprises an acoustic intensity of a mechanic index value.

8. A method in accordance with claim 5 wherein the control parameter comprises at least one of an average intensity value, an average mechanic index value, an averaged intensity value in a region of interest, and a root mean square intensity value.

9. A method in accordance with claim 8 wherein the determining, comparing, and adjusting steps are repeated until the actual value of the control parameter is value is less than the threshold value.

10. A method in accordance with claim 1 further comprising performing a contrast imaging scan and wherein iteratively adjusting an acoustic power output comprises automatically setting the acoustic power to a level based on at least one characteristic of the object as determined by the acquired ultrasound data such that the power level minimizes destruction of contrast bubbles within the object.

11. A method for controlling power in an ultrasound system, said method comprising:
    performing a contrast imaging setting scan of an object including scanning the object with a first acoustic power output;
    determining an acoustic power output based on ultrasound data acquired from a region of interest of the object being scanned during the contrast imaging setting scan; and
    iteratively setting the acoustic power output of the ultrasound system based on the acquired ultrasound data from the contrast imaging setting scan, wherein iteratively setting the acoustic power output comprises:
    determining a difference between an actual acoustic power output and a threshold acoustic power output; and
    adding the determined difference to the first acoustic power output to generate a second acoustic power output.

12. A method in accordance with claim 11 wherein the threshold acoustic power output comprises a predetermined threshold value of a control parameter, and wherein determining an acoustic power output comprises using the predetermined threshold value and the acquired ultrasound data from the contrast imaging setting scan of the object to establish the acoustic power output for scanning the object in a contrast imaging scanning mode.

13. A method in accordance with claim 12 wherein the ultrasound data comprises an acoustic intensity value relating to the region of interest and further comprising iteratively performing the contrast imaging setting scan of the object until the acoustic intensity value is less than the predetermined threshold value.

14. A method in accordance with claim 12 wherein the predetermined threshold value is based on clinical analysis of a plurality of objects having different characteristics.

15. A method in accordance with claim 12 further comprising calculating a control parameter value related to a mechanic index value based on the acquired ultrasound data and comparing the calculated control parameter value to the predetermined threshold value to determine if the calculated control parameter value is less than the predetermined threshold value.

16. A method in accordance with claim 11 wherein iteratively setting the acoustic power output comprises iteratively setting the acoustic power output before injecting a contrast agent into the object.

17. An ultrasound system comprising:

a scanning portion for scanning an object; and a control portion configured to:

receive first ultrasound data relating to the object from the scanning portion;

make a first adjustment of an acoustic power output of the scanning portion based on the received first ultrasound data;

receive second ultrasound data relating to the object from the scanning portion, the second ultrasound data relating to the object after the first adjustment; and make a second adjustment of the acoustic power output of the scanning portion based on the received second ultrasound data, wherein the control portion is configured to make at least one of the first and second adjustments by determining a difference in the acoustic power output and adjusting the acoustic power output based on the determined difference.

* * * * *